(12) United States Patent
Kim et al.

(10) Patent No.: US 10,324,016 B2
(45) Date of Patent: Jun. 18, 2019

(54) METHOD FOR MEASURING METAL ION PERMEABILITY OF POLYMER FILM AND DEVICE FOR MEASURING METAL ION PERMEABILITY OF POLYMER FILM

(71) Applicant: LG CHEM, LTD., Seoul (KR)

(72) Inventors: Young Kook Kim, Daejeon (KR); Jung Hak Kim, Daejeon (KR); Hee Jung Kim, Daejeon (KR); Se Ra Kim, Daejeon (KR); Jung Ho Jo, Daejeon (KR); Kwang Joo Lee, Daejeon (KR); Seung Hee Nam, Daejeon (KR); Ji Ho Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/529,787

(22) PCT Filed: Jan. 29, 2016

(86) PCT No.: PCT/KR2016/001022
§ 371 (c)(1),
(2) Date: May 25, 2017

(87) PCT Pub. No.: WO2016/122264
PCT Pub. Date: Aug. 4, 2016

(65) Prior Publication Data
US 2017/0336315 A1    Nov. 23, 2017

(30) Foreign Application Priority Data

Jan. 29, 2015  (KR) ........................ 10-2015-0014306
Jan. 29, 2015  (KR) ........................ 10-2015-0014307

(51) Int. Cl.
*G01R 15/08*   (2006.01)
*G01N 27/04*   (2006.01)
(Continued)

(52) U.S. Cl.
CPC ....... *G01N 15/0806* (2013.01); *G01N 27/041* (2013.01); *G01N 27/3335* (2013.01); *G01N 2013/003* (2013.01); *G01N 2015/086* (2013.01)

(58) Field of Classification Search
CPC ........ G01R 15/08; G01R 27/08; G01N 27/04; G01N 27/06; G01N 27/12; G01N 27/14; G01N 27/404; G01N 27/62; B23H 5/00
See application file for complete search history.

(56) References Cited

U.S. PATENT DOCUMENTS 4,454,007 A    6/1984   Pace
4,871,427 A    10/1989  Kolesar, Jr.
(Continued)

FOREIGN PATENT DOCUMENTS

CN    86107737 A     6/1987
CN    101246095 A    8/2008
(Continued)

OTHER PUBLICATIONS

Search Report and Written Opinion issued for International Application No. PCT/KR2016/001022 dated Apr. 19, 2016 (20 pages).
(Continued)

*Primary Examiner* — Neel D Shah
(74) *Attorney, Agent, or Firm* — Rothwell, Figg, Ernst & Manbeck, P.C.

(57) ABSTRACT

The present invention relates to a method for measuring metal ion permeability of a polymer film, comprising the steps of applying a voltage to the polymer film, while at least one side of the polymer film is brought into contact with an electrolyte comprising metal ions, an organic solvent and an aqueous solvent; and measuring the change rate of resistance or change rate of current of the polymer film according to (Continued)

time, after the voltage is applied, and a device for measuring metal ion permeability of a polymer film used therefor.

25 Claims, 5 Drawing Sheets

(51) Int. Cl.

| | |
|---|---|
| *G01N 27/06* | (2006.01) |
| *G01N 27/12* | (2006.01) |
| *G01N 27/14* | (2006.01) |
| *G01N 27/62* | (2006.01) |
| *G01N 15/08* | (2006.01) |
| *G01N 27/333* | (2006.01) |
| *G01N 13/00* | (2006.01) |

(56) References Cited

U.S. PATENT DOCUMENTS

| | | | |
|---|---|---|---|
| 8,358,137 B2 | 1/2013 | Uchiyama | |
| 8,674,349 B2 | 3/2014 | Shinoda et al. | |
| 8,735,881 B1 | 5/2014 | Shinoda et al. | |
| 2006/0157355 A1* | 7/2006 | Baskaran | C25D 3/02 205/674 |
| 2011/0001500 A1 | 1/2011 | Uchiyama | |
| 2012/0175604 A1 | 7/2012 | Hanna et al. | |
| 2014/0370404 A1 | 12/2014 | Kato et al. | |
| 2017/0038324 A1 | 2/2017 | Suzumura et al. | |
| 2017/0328851 A1* | 11/2017 | Kim | G01N 27/447 |

FOREIGN PATENT DOCUMENTS

| | | |
|---|---|---|
| CN | 101995430 B | 8/2012 |
| DE | 102005040592 A1 | 3/2007 |
| JP | 03-085440 A | 4/1991 |
| JP | 06-317560 A | 11/1994 |
| JP | H07-130809 A | 5/1995 |
| JP | 2002-156359 A | 5/2002 |
| JP | 2005-009938 A | 1/2005 |
| JP | 2009-081127 A | 4/2009 |
| JP | 4680630 B2 | 5/2011 |
| KR | 10-2000-0006773 A | 2/2000 |
| KR | 20-0258792 Y1 | 12/2001 |
| KR | 20-0288338 Y1 | 9/2002 |
| KR | 10-2010-0038358 A | 4/2010 |
| KR | 10-2010-0041748 A | 4/2010 |
| KR | 10-2012-0081093 A | 7/2012 |
| KR | 10-1311661 B1 | 9/2013 |
| KR | 10-2014-0088889 A | 7/2014 |

OTHER PUBLICATIONS

Burgmayer, P. et al., "An Ion Gate Membrane: Electrochemical Control of Ion Permeability through a Membrane with an Embedded Electrode", Journal of American Chemistry Society, vol. 104, 1982, p. 6139-6140.

* cited by examiner

METHOD FOR MEASURING METAL ION PERMEABILITY OF POLYMER FILM AND DEVICE FOR MEASURING METAL ION PERMEABILITY OF POLYMER FILM

CROSS-REFERENCE TO RELATED APPLICATIONS

This application is a 35 U.S.C. § 371 National Phase Entry Application from PCT/KR2016/001022, filed on Jan. 29, 2016, and designating the United States, which claims priority under 35 U.S.C. § 119 to Korean Patent Application No. 10-2015-0014306 filed on Jan. 29, 2015 and Korean Patent Application No. 10-2015-0014307 filed on Jan. 29, 2015 with the Korean Intellectual Property Office, the disclosures of which are herein incorporated by reference in their entirety.

TECHNICAL FIELD OF THE INVENTION

The present invention relates to a method for measuring metal ion permeability of a polymer film and a device for measuring metal ion permeability of a polymer film, more specifically, to a method for measuring metal ion permeability of a polymer film and a device for measuring metal ion permeability of a polymer film that can more easily and correctly measure metal ion permeability of a polymer film used in a semiconductor device, etc., and can reduce the time required for measuring, and improve efficiency.

BACKGROUND OF THE INVENTION

Metal ion permeability of a polymer film used in a semiconductor device or a display device is an important factor for securing the reliability of the material used or final products. However, a method capable of directly measuring metal ion permeability of a polymer film is not widely known, and according to previously known measurement methods, a complicated multistage process should be conducted, and the resulting measurement reliability of metal ion permeability of a polymer film is not so high.

For example, previously, a method of introducing a polymer film to be measured into a metal ion solution and heating, and then, calculating the weight of metal ions adsorbed to the polymer film was used; however, it was difficult to consider the obtained measurement result as metal ion permeability. And, as another measurement method previously known, a method of diffusing a copper precursor into a wafer, and then, combining a polymer film to be measured on the wafer to re-diffuse the copper precursor, and quantifying the amount of copper ions contained in the polymer film is known. However, according to this method, the pretreatment process and quantification process are complicated, and an excessive amount of toxic material such as hydrofluoric acid, etc. should be used.

(Patent Document 1) Korean Registered Patent No. 1311661

SUMMARY OF THE INVENTION

It is an object of the present invention to provide a method for measuring metal ion permeability of a polymer film that can more easily and correctly measure metal ion permeability of a polymer film used in a semiconductor device, etc., and can reduce a time required for measuring and thus has improved efficiency.

It is another object of the present invention to provide a device for measuring metal ion permeability of a polymer film that can more easily and correctly measure metal ion permeability of a polymer film used in a semiconductor device, etc., and can reduce a time required for measuring and thus has improved efficiency.

A method for measuring metal ion permeability of a polymer film, comprising the steps of applying a voltage to the polymer film, while at least one side of the polymer film is brought into contact with an electrolyte comprising metal ions, an organic solvent and an aqueous solvent; and measuring the change rate of resistance or change rate of current of the polymer film according to time, after the voltage is applied, is provided herein.

The step of measuring the change rate of resistance or change rate of current of the polymer film according to time, after the voltage is applied, may comprise a step of measuring a time until a first time (T) at which the change rate of current or resistance according to time is constantly maintained, after the voltage is applied.

The first time at which the change rate of current or resistance according to time is constantly maintained, may be the first time of a time interval in which the change rate of current or the change rate of resistance according to time is included in a range within 25% of a mean value of the change rate of current or the change rate of resistance according to time, or the first time at which the change ratio of the differential value of change of current or resistance according to time becomes 0, after passing an inflection point of change of current or resistance according to time.

The metal ion permeability of the polymer film may be defined as a average rate of change of current or the change rate of resistance according to time, after the first time (T).

The time until the first time (T) at which the change rate of current or resistance according time is constantly maintained, after the voltage is applied, may be 8 hours or less.

The time until the first time (T) at which the change rate of current or resistance according time is constantly maintained, after the voltage is applied, may be measured at room temperature, atmospheric pressure and an applied voltage of 10V.

The electrolyte may comprise the organic solvent in an amount of 20 to 200 parts by weight, based on 100 parts by weights of the aqueous solvent.

The boiling point of the organic solvent included in the electrolyte may be higher than the temperature of the step of applying a voltage to the polymer film.

The organic solvent included in the electrolyte may comprise a sulfoxide organic solvent. The sulfoxide organic solvent may comprise dialkyl sulfoxide having a carbon number of 1 to 3.

The concentration of the metal ions included in the electrolyte may be 0.1 ppmw to 2,000 ppmw.

The metal ions may include one or more metal ions selected from the group consisting of copper, gold, platinum, silver, iron, mercury, potassium, calcium, sodium, aluminum, nickel and chromium.

The step of applying a voltage to the polymer film while at least one side of the polymer film is brought into contact with an electrolyte comprising metal ions, an organic solvent and an aqueous solvent, may comprise the step of applying a voltage while one side of the polymer film is brought into contact with an electrolyte comprising metal ions.

The step of applying a voltage while one side of the polymer film is brought into contact with an electrolyte comprising metal ions, may comprise the step of applying voltages to a first electrode that is in contact with the other side of the polymer film, and to a second electrode that opposes the first electrode and is in contact with the electrolyte.

The step of applying a voltage while at least one side of the polymer film is brought into contact with an electrolyte comprising metal ions, may comprise the step of applying a voltage to the polymer film, while one side of the polymer film is brought into contact with a first electrolyte comprising metal ions and the other side of the polymer film is brought into contact with a second electrolyte.

The step of applying a voltage to the polymer film, while one side of the polymer film is brought into contact with a first electrolyte comprising metal ions and the other side of the polymer film is brought into contact with a second electrolyte, may comprise the step of applying voltages to a first electrode that is in contact with the first electrolyte comprising metal ions, and a second electrode that opposes the first electrode and is in contact with the second electrolyte.

The metal ions included in the first electrolyte and the second electrolyte may be different from each other, and the concentrations of the metal ions included in the first electrolyte and the second electrolyte may be respectively 0.1 ppmw to 2,000 ppmw.

The step of applying a voltage to the polymer film while at least one side of the polymer films is brought into contact with an electrolyte comprising metal ions, may further comprise a step of applying a voltage to the polymer film at a temperature of 5° C. to 250° C.

And, a device for measuring metal ion permeability comprising: a first electrode and a second electrode opposing each other; an electrolyte compartment that is in contact with the first electrode, and includes an electrolyte comprising metal ions, an organic solvent and an aqueous solvent inside; a polymer film mounting part that is positioned between the second electrode and the electrolyte compartment, and is installed in such a way that the electrolyte included in the electrolyte compartment is in contact with a polymer resin film; a voltage applying part that is connected with the first electrode and the second electrode, and applies a voltage; and an electrical signal measuring part that measures resistance change or current change of the polymer film mounted in the polymer film mounting part, is also provided herein.

The polymer film mounting part may be installed in such a way that one side of the second electrode is in contact with a polymer resin film. The polymer film mounting part may further comprise a fixing tool that closely contacts the second electrode, the polymer film mounted on the polymer film mounting part, and the electrolyte compartment with one another, and fixes them.

The device may further comprise a second electrolyte compartment that is positioned between the second electrode and the polymer film mounting part, is in contact with the second electrode, and includes an electrolyte comprising metal ions, an organic solvent and an aqueous solvent. The electrolyte included in the second electrolyte compartment may comprise 0.1 ppmw to 2,000 ppmw of metal ions. The metal ions in the electrolyte included in the second electrolyte compartment may be different from the metal ions in the electrolyte included in the electrolyte compartment. The polymer film mounting part may further comprise a fixing tool that closely contacts the first electrolyte compartment, the second electrolyte compartment, and the polymer film mounted on the polymer film mounting part with one another, and fixes them.

The device may further comprise a chamber including an internal space in which the first electrode, second electrode, electrolyte compartment and polymer film mounting part are positioned. The chamber may further comprise a temperature control part and a humidity control part.

The electrical signal measuring part is a device that measures the change rate of resistance or change rate of current according to time of the polymer film mounted on the polymer film mounting part, after applying voltages to the first electrode and the second electrode using the voltage applying part.

And, a device for measuring metal ion permeability of a polymer film, for use in the above-explained method for measuring metal ion permeability of a polymer film, is also provided herein.

According to the present invention, a method for measuring metal ion permeability of a polymer film and a device for measuring metal ion permeability of a polymer film that can more easily and correctly measure metal ion permeability of a polymer film used in a semiconductor device, etc., and reduce a time required for measuring and thus have improved efficiency can be provided.

DETAILED DESCRIPTION OF THE INVENTION

Figure 1:
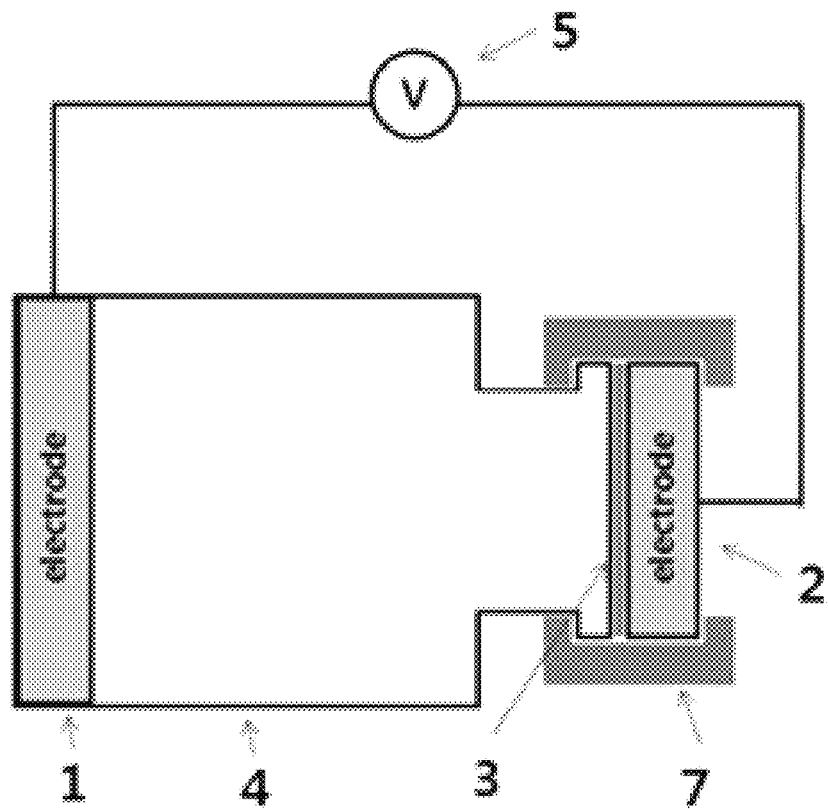
FIG. 1 schematically shows one example of a device for measuring metal ion permeability of a polymer film of the present invention.

Hereinafter, a method for measuring metal ion permeability of a polymer film and a device for measuring metal ion permeability of a polymer film according to specific embodiments of the present invention will be explained in more detail.

According to one embodiment of the present invention, a method for measuring metal ion permeability of a polymer film, comprising the steps of applying a voltage to the polymer film, while at least one side of the polymer film is brought into contact with an electrolyte comprising metal ions, an organic solvent and an aqueous solvent; and measuring the change rate of resistance or change rate of current of the polymer film according to time, after the voltage is applied, is provided.

It is known that, metal impurities in a semiconductor device or display device, etc. have a fatal influence on the physical and electrical properties of the electrical electronic device, and thus, significantly reduce manufacturing reliability and yield, etc. Specifically, metal or metal ions diffuse into a device such as a semiconductor substrate, etc. at high temperature and is positioned at a deep level in a silicon forbidden bandgap, thus acting as a trap center that causes production and recombination of a few carriers, thereby decreasing the lifespan of a few carriers, increasing leakage current of p-n junctions, and decreasing the breakdown voltage of oxides.

Since parts of polymer films used in a semiconductor device or display device, etc., for example, a die bonding film, a solder resist, a bonding sheet for a substrate, an insulation film, etc. have insulation properties, it is not easy to measure metal permeability or metal ion permeability of the polymer resin film, or evaluate related performances.

Thus, the present inventors confirmed through experiments that by applying a voltage while both sides of a polymer film used in a semiconductor device, etc. are brought into contact with predetermined electrolytes, and after applying the voltage, measuring the change of resistance or change of current of the polymer film, metal ion permeability of the polymer film to be measured can be more correctly and easily measured, and completed the present invention.

Particularly, in the measurement method of metal ion permeability of the above embodiment, even in case two or more electrolytes are used, since all the electrolytes comprise metal ions, organic solvents and aqueous solvents, the flowability of current by the electrolytes can be improved. Thus, a fine current flow change that is generated in case a trace amount of metal ions penetrate a polymer insulation film can be easily measured with high reproducibility.

Specifically, the metal ion permeability of a polymer film may be determined as a time until the first time (T) at which the change rate of current or resistance according to time is constantly maintained, from the time at which a predetermined voltage (for example, 0.1 V to 10.0 V) is applied.

The meaning of the description "the change rate of current or resistance according to time is constantly maintained" includes a case wherein, in the corresponding time interval, the change rate of current or resistance according to time is included in a range within 25% of the mean value of the change rate of current or the change rate of resistance according to time, and a case wherein the change ratio of instantaneous rate of change of current or resistance according to time (or the change ratio of the differential value of change of current or resistance according to time) becomes 0, etc.

The first time (T) at which the change rate of current or resistance according time is constantly maintained means a first time at which the change of current or resistance according to time becomes constant, after the change of current or resistance according time occurs, and it may appear after passing an inflection point of the change of current or resistance according to time.

The first time (T) may be determined as a first time at which the change ratio of the instantaneous rate of change of current or resistance according to time (or the change ratio of the differential value of current or resistance change according to time) becomes 0, or as a first time in a time interval in which the change rate of current or resistance according to time is included in a range within 25% of the mean value of the change rate of current or the change rate of resistance according to time.

For the determination of the first time, various methods can be used without specific limitations, and for example, it may be determined by calculating the average change rate of current or resistance according to time in a corresponding time interval, and extrapolating a time at which the average change rate value appears, after passing an inflection point of current or resistance change according to time.

Although the range of change rate of current or change rate of resistance that can be measured by the measurement method of metal ion permeability of a polymer film of the above embodiment is not significantly limited, for example, in case a voltage of 0.1 V to 10.0 V is applied, the first time at which the change of current or resistance becomes constant, after change of current or resistance according to time occurs, may be 8 hours or less, or 0.5 hours to 8 hours.

More specifically, a time until the first time (T) at which the change rate of current or resistance according to time is constantly maintained after the voltage is applied, may be measured at room temperature, atmospheric pressure and an applied voltage of 10V. The room temperature indicates a temperature of about 25° C., and the atmospheric pressure indicates a pressure of about 1 atm.

Meanwhile, the metal ion permeability may be represented by the change rate of current or voltage according to time, and specifically, it may be the average rate of change of current or the change rate of resistance according to time, after the first time (T), and for example, it may be A/10 seconds, A/1 minutes, A/1 hours, A/10 hours, $\Omega$/10 seconds, $\Omega$/1 minutes, $\Omega$/1 hours, $\Omega$/10 hours, etc.

In the measurement method of metal ion permeability of a polymer film of the above embodiment, the measuring device of the change rate of current or change rate of voltage is not significantly limited in terms of its kind or structure, any device capable of measuring the change of current or change of voltage occurred in a polymer film to be measured, after applying a voltage, may be used without significant limitations, and for example, devices such as a potentiostat, etc. may be used.

The size of the voltage applied to the polymer film may be selected within a range of 0.001 V to 100 V, considering the kind of the polymer film or the measured value of current change or voltage change.

And, the electrolyte may comprise metal ions, an organic solvent and an aqueous solvent.

The electrolyte may comprise 20 to 200 parts by weight, or 30 to 150 parts by weight, or 40 to 100 parts by weight of the organic solvent, based on 100 parts by weight of the aqueous solvent.

In the electrolyte, if the content of the organic solvent is excessively decreased to less than 20 parts by weight, based on 100 parts by weight of the aqueous solvent, due to decrease in the penetration speed of metal ions and the resulting increase in the measuring time of metal ion permeability, in case a voltage of 0.1 V to 10.0 V is applied in a measuring device, the first time at which the change of current or resistance according to time becomes constant after the change of current or resistance according to time occurs may be increased to become greater than 10 hours, and thus, measuring efficiency may be decreased.

And, if the content of the organic solvent is excessively increased to greater than 200 parts by weight, based on 100 parts by weight of the aqueous solvent, the polymer film may be excessively swollen by the organic solvent and thus may be damaged, and the penetration time of metal ions may become too short, thus rendering it difficult to reproducibly measure the metal ion permeability of the polymer film itself.

The boiling point of the organic solvent included in the electrolyte may be higher than the temperature of the step of applying a voltage to the polymer film. More specifically, the boiling point of the organic solvent included in the electrolyte may be 10° C. to 300° C., or 50° C. to 200° C. higher than the temperature of the step of applying a voltage to the polymer film.

If the boiling point of the organic solvent included in the electrolyte is higher than the temperature of the step of applying a voltage to the polymer film by less than 10° C., during warming using a chamber, the organic solvent may be volatilized.

And, if the boiling point of the organic solvent included in the electrolyte is higher than the temperature of the step of applying a voltage to the polymer film by greater than 300° C., as the warming temperature using a chamber increases, the transfer rate of metal ions increases, thus generating excessive pressure inside a compartment, and thus, there is a concern about damage of the polymer film.

More specifically, the boiling point of the organics solvent included in the electrolyte may be 100° C. to 200° C., or 150° C. to 200° C., or 170° C. to 200° C., and the temperature of the step of applying a voltage to the polymer film may be 5° C. to 250° C., or 20° C. to 200° C.

The organics solvent included in the electrolyte may include sulfoxide organic solvents. The sulfoxide organic solvents has a moiety including a sulfinyl (—SO—) group in the molecular structure, and aliphatic, alicyclic, or aromatic hydrocarbon functional groups, respectively independently substituted or unsubstituted, may be bonded to both ends of the sulfinyl group.

The term "substituted or unsubstituted" means to include the functional groups further substituted with specific substituents, as well as each functional group itself. As used herein, unless otherwise defined, examples of the substituents that can be further substituted may include halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, siloxy, or "polar functional groups including oxygen, nitrogen, phosphorus, sulfur, silicon or boron" as explained above, etc.

More specifically, the sulfoxide organic solvent may include dialkyl sulfoxide having a carbon number of 1 to 3. The dialkyl sulfoxide having a carbon number of 1 to 3 may be a compound in which unsubstituted aliphatic hydrocarbon functional groups, for example, C1-3 alkyl groups, are respectively bonded to both ends of a sulfinyl group. Preferable example of the dialkyl sulfoxide having a carbon number of 1 to 3 may include dimethyl sulfoxide.

As such, the sulfoxide organic solvent that is used as the organic solvent included in the electrolyte has very high polarity and thus may have a high miscibility with the aqueous solvent, and may improve the transfer rate of metal ions in the electrolyte, thus remarkably reducing the measurement time of metal ion permeability.

And, the sulfoxide organic solvent that is used as the organic solvent included in the electrolyte has weak toxicity compared to the previously used N-methypyrrolidone (NMP), and thus, is favorable in terms of pro-environmental aspects.

Besides, as the organic solvent, one kind or two or more kinds of common organic solvents known to be usable as an electrolyte may be mixed and used, and examples of the organic solvents may include alcohols such as methanol, ethanol, propanol, iso-propanol, butanol, or pentanol, acids such as acetic acid, nitric acid or hydrochloric acid, etc., n-methyl pyrrolidone (NMP), acetone, dimethylformamide, tetrahydrofurane (THF), dioxane, dimethylacetamide, polyethyleneglycol (PEG), xylene, toluene, chloroform, etc., but are not limited thereto.

As the aqueous solvent, water may be used.

The metal ion may include one or more ions of metal selected from the group consisting of copper, gold, platinum, silver, iron, mercury, potassium, calcium, sodium, aluminum, nickel and chromium.

And, although the concentration of the electrolyte comprising the metal ions is not significantly limited, in order to facilitate the operation of the device for measuring metal ion permeability of a polymer film and more clearly measure the metal ion permeability, it is preferable that electrolyte with the concentration of metal ions of 0.1 ppmw to 2,000 ppmw stays in the electrolyte compartment (4).

Although the method of including the metal ions in the electrolyte is not significantly limited, for example, a method of mixing metal salts containing the metal ions with an aqueous solvent and an organic solvent, etc. may be used.

Thus, the electrolyte may further comprise anions. The anion means a negatively (−) charged ion, and it may combine with the metal ions and exist in the form of a metal salt, or may be separated from the metal ions and exist in the form of a separate anion. That is, as explained above, in case a method of mixing metal salts containing metal ions with an aqueous solvent and an organic solvent is used, anions derived from the metal salt may remain in the electrolyte.

The examples of the anions are not significantly limited, and for example, may include sulfate ion ($SO_4^{2-}$), nitrate ion ($NO_3^-$), perchlorate ion ($ClO_4^-$), halogenated ion ($F^-$, $Br^-$, $Cl^-$, $I^-$), hydroxide ion ($OH^-$), acetate ion ($CH_3COO^-$), etc., and preferably, sulfate ion ($SO_4^{2-}$).

In case the sulfate ion ($SO_4^{2-}$) is contained in the electrolyte, due to its structural similarity to the above explained sulfoxide organic solvents used as an organic solvent, miscibility in the electrolyte may be further improved, and thus, mobility of metal ions may become fast, thus remarkably reducing the measurement time of metal ion permeability.

The concentration of the anions may be identical to the above explained concentration of metal ions, or it may be higher or lower than the concentration of metal ions so as to charge balance with the quantity of electric charge of metal ions. And, the anion may exist in the form of a separate anion in the electrolyte, or it may react with an aqueous solvent and exist in the form of a hydrate or acid.

More specifically, as the electrolyte, a first solution containing copper ions or a second solution containing sodium ions may be used, wherein the first solution containing copper ions may comprise copper ions, an organic solvent and an aqueous solvent, and the second solution containing sodium ions may comprise sodium ions, an organic solvent and an aqueous solvent. The above explained applies to the organic solvent and the aqueous solvent. And, the concentration of copper ions in the first solution may be 0.1 ppmw to 2,000 ppmw, and the concentration of sodium ions in the second solution may be 0.1 ppmw to 2,000 ppmw.

Meanwhile, the step of applying a voltage to the polymer film while at least one side of the polymer film is brought into contact with an electrolyte comprising metal ions, may comprise a step of applying a voltage while one side of the polymer film is brought into contact with an electrolyte comprising metal ions.

Here, only one side of the polymer film may contact with the electrolyte, and the opposite side of the polymer film may not contact with the electrolyte but contact with a second electrode. The opposite side means another side that is parallel to one side contacting with the electrolyte. As such, by contacting one side of the polymer film with the electrolyte and directly contacting the opposite side with the second electrode, the polymer film may be supported to realize structural stability.

The step of applying a voltage while one side of the polymer film is brought into contact with an electrolyte comprising metal ions, may comprise a step of applying voltages to a second electrode that is in contact with the other side of the polymer film, and to a first electrode that opposes the second electrode and is in contact with the electrolyte.

Here, the electrolyte may comprise 0.1 ppmw to 2,000 ppmw of metal ions, and for example, as the electrolyte, a first solution comprising copper ions or a second solution comprising sodium ions may be used, and preferably, a first solution comprising copper ions may be used. The above explained applies to the first solution and the second solution.

And, the step of applying a voltage to the polymer film while at least one side of the polymer film is brought into contact with an electrolyte comprising metal ions, may comprise a step of applying a voltage to the polymer film while one side of the polymer film is brought into contact with a first electrolyte comprising metal ions and the other side of the polymer film is brought into contact with a second electrolyte.

Here, the first electrolyte and second electrolyte may respectively comprise 0.1 ppmw to 2,000 ppmw metal ions, and the metal ions included in the first electrolyte and second electrolyte may be different from each other.

Specifically, as the first electrolyte, a first solution comprising copper ions may be used, and as the second electrolyte, a second solution comprising sodium ions may be used. The above explained applies to the first solution and second solution.

The step of applying a voltage to the polymer film while one side of the polymer film is brought into contact with a first electrolyte comprising metal ions and the other side of the polymer film is brought into contact with a second electrolyte, may comprise a step of applying a voltage to a first electrode that is in contact with the first electrolyte comprising metal ions and to a second electrode that opposes to the first electrode and is in contact with the second electrolyte.

The step of applying a voltage to the polymer film while at least one side of the polymer film is brought into contact with the first electrolyte comprising metal ions, may comprise a step of applying a voltage to the polymer film at a temperature of 5° C. to 250° C., or 20° C. to 200° C. A method of controlling the temperature to 5° C. to 250° C., or 20° C. to 200° C. is not significantly limited, and for example, a chamber may be used.

As the chamber, reaction chambers made of commonly known material may be used, and the shape or structure of the chamber is not significantly limited.

And, the chamber may further comprise a temperature control part and a humidity control part.

The temperature inside the chamber may be 0° C. to 400° C., and through the temperature control part, the temperature may be controlled in the process of measuring metal ion permeability of a polymer film. Specific structure or kind of the temperature control part is not significantly limited, and for example, devices such as a convection oven, a HAST ([Highly Accelerated Stress Test] oven or a PCT (Pressure Cooker Test) oven, etc. may be used.

In case the device for measuring of metal ion permeability of a polymer film is operated to measure metal ion permeability, the temperature inside the chamber may be 5° C. to 250° C., or 20° C. to 200° C.

In case the device for measuring of metal ion permeability of a polymer film is operated to measure metal ion permeability, the pressure inside the chamber may be 1 atm to 5 atm.

Meanwhile, according to another embodiment of the present invention, a device for measuring metal ion permeability of a polymer film comprising: a first electrode and a second electrode opposing each other; an electrolyte compartment that is in contact with the first electrode, and includes an electrolyte comprising metal ions, an organic solvent and an aqueous solvent inside; a polymer film mounting part that is positioned between the second electrode and the electrolyte compartment, and is installed in such a way that the electrolyte included in the electrolyte compartment is in contact with a polymer resin film; a voltage applying part that is connected with the first electrode and the second electrode, and applies a voltage; and an electrical signal measuring part that measures resistance change or current change of the polymer film mounted in the polymer film mounting part, is provided.

The present inventors confirmed through experiments that by applying a voltage while at least one side of a polymer film used in a semiconductor device, etc. is brought into contact with a predetermined electrolyte, and after applying the voltage, measuring the change of resistance or change of current of the polymer film, metal ion permeability of the polymer film to be measured can be more correctly and easily measured, and based thereon, invented a device for measuring metal ion permeability of a polymer film and completed the present invention.

Specifically, the detailed structure of the device for measuring metal ion permeability of a polymer film of the above embodiment is as follows.

The device for measuring metal ion permeability of a polymer film comprises a first electrode and a second electrode opposing each other. As the first electrode (1) and second electrode (2), common electrodes known to be used in a secondary battery, etc. may be used, and for example, copper, aluminum lithium, platinum, gold, iron, zinc, nickel, silver, lead, carbon electrodes, ITO or PEDOT/PSS, etc. may be used. The first electrode (1) and second electrode (2) oppose each other.

The device for measuring metal ion permeability of a polymer film comprises an electrolyte compartment that is in contact with the first electrode, and includes an electrolyte comprising metal ions, an organic solvent and an aqueous solvent inside. That is, the electrolyte included inside the electrolyte compartment may be in contact with the first electrode and comprise metal ions, an organic solvent and an aqueous solvent.

Specifically, examples of the method of contacting the electrolyte with the first electrode inside the electrolyte compartment is not significantly limited, and for example, a method of impregnating the first electrode with the electrolyte compartment including the electrolyte inside, or a method of contacting the electrolyte compartment with one side of the first electrode, so that a space defined by a partition wall (side wall) connecting the first electrode (1) and the polymer film mounting part (3) may become the electrolyte compartment, etc. may be used.

And, the electrolyte positioned in the electrolyte compartment may comprise metal ions, an organic solvent and an aqueous solvent. The above explained applies to the electrolyte, metal ion, organic solvent and aqueous solvent.

The material of the partition wall (side wall) of the electrolyte compartment (4) is not significantly limited, and it may comprise material having high stability to electrolyte staying inside, and having stability under temperature and pressure conditions applied in the process of measuring metal ion permeability. Specifically, the partition wall (side wall) of the electrolyte compartment may include materials such as glass, Teflon, or polymer, etc., but specific examples are not limited thereto.

And, although the thickness of the partition wall of the electrolyte compartment is not significantly limited, for example, it may have a thickness of 1 mm to 500 mm The device for measuring metal ion permeability of a polymer film comprises a polymer film mounting part (3) that is positioned between the second electrode (2) and the electrolyte compartment (4), and is installed in such a way that the electrolyte included in the electrolyte compartment is in contact with a polymer resin film.

The polymer film mounting part (3) positioned between the second electrode (2) and the electrolyte compartment (4) may be defined as a space formed between the second electrode (2) and the electrolyte compartment (4), and it may also be defined as a separate mounting device or fixing device installed in the space. For example, the polymer film mounting part (3) may be a space of a spherical shape, circular shape, or polygon of which cross section has 3 to 20 internal angles, and may comprise a glass filter or a polymer film support part of a mesh shape.

Specifically, the polymer film mounting part may be installed in such a way that one side of the second electrode is in contact with the polymer resin film. Thus, if a polymer film of which metal ion permeability is to be measured is positioned on the polymer film mounting part (3), electrolyte comprising metal ions in the electrolyte compartment (4) contacts with one side of the polymer film. And, while one side of the polymer film is brought into contact with the electrolyte comprising metal ions, voltages are applied to the second electrode that is in contact with the other side of the polymer film and to the first electrode that opposes the second electrode and is in contact with the electrolyte, using a voltage applying part (5) that is connected to the first electrode and second electrode and applies voltages, and thereafter, the change of voltage or change of current of the polymer film mounted on the polymer film mounting part is measured using an electrical signal measuring part (6).

And, the polymer film mounting part may further comprise a fixing tool that closely contacts the second electrode, the polymer film mounted on the polymer film mounting part, and the electrolyte compartment with each other, and fixes them. Specific shape or practical fastening method or structure of the fixing tool (7) is not significantly limited, and for example, a fixing tool (jig) of a structure that can be added to the rear side of the external protrusion part of the polymer film mounting part may be used, a hole penetrating the fixing tool and the external protrusion part of the polymer film mounting part may be connected with a screw to press, and both ends of a belt-shaped structure with a groove of an oblique angle covering the external protrusion part of the polymer film mounting part may be fixed with a screw to press.

Meanwhile, the device for measuring metal ion permeability may further comprise a second electrolyte compartment that is positioned between the second electrode and the polymer film mounting part, is in contact with the second electrode, and includes an electrolyte comprising metal ions, an organic solvent and an aqueous solvent inside. That is, the electrolyte included inside the second electrolyte compartment is in contact with the second electrode, and may comprise metal ions, an organic solvent and an aqueous solvent.

Specifically, examples of the method by which an electrolyte is brought in contact with a second electrode in the second electrolyte compartment are not significantly limited, and for example, may include a method of impregnating the second electrode with the electrolyte compartment including the electrolyte inside or a method of contacting the second electrolyte compartment with one side of the second electrode, so that a space defined by the partition walls (side walls) connecting the second electrode (2) and the polymer film mounting part (3) may become an electrolyte compartment, etc.

More specifically, the device for measuring metal ion permeability of a polymer film may comprise a first electrode and a second electrode opposing each other; a first electrolyte compartment that is in contact with the first electrode, and includes an electrolyte comprising metal ions, an organic solvent and an aqueous solvent inside; a polymer film mounting part that is positioned between the second electrode and the electrolyte compartment, and is installed in such a way that the electrolyte included in the electrolyte compartment is in contact with a polymer resin film; a second electrolyte compartment that is positioned between the second electrode and the polymer film mounting part, is in contact with the second electrode, and includes an electrolyte comprising metal ions, an organic solvent and an aqueous solvent inside; a voltage applying part that is connected with the first electrode and the second electrode, and applies a voltage; and an electrical signal measuring part that measures resistance change or current change of the polymer film mounted in the polymer film mounting part.

The electrolyte included in the second electrolyte compartment may comprise 0.1 ppmw to 2,000 ppmw of metal ions. The metal ion may include one or more ions of metal selected from the group consisting of copper, gold, platinum, silver, iron, mercury, potassium, calcium, sodium, aluminum, nickel and chromium.

And, although the concentration of the electrolyte comprising the metal ions is not significantly limited, in order to facilitate the operation of the device for measuring metal ion permeability of a polymer film and more clearly measure the metal ion permeability, it is preferable that electrolyte with the concentration of metal ions of 0.1 ppmw to 2,000 ppmw stays in the second electrolyte compartment (8).

The metal ions in the electrolyte included in the second electrolyte compartment may be different from the metal ions in the electrolyte included in the electrolyte compartment (first electrolyte compartment).

For specific examples, the device for measuring metal ion permeability of a polymer film may comprise a first electrolyte comprising copper ions in the first electrolyte compartment, and a second electrolyte comprising sodium ions in the second electrolyte compartment, and the first electrolyte may comprise 0.1 ppmw to 2,000 ppmw of copper ions and the second electrolyte may comprise 0.1 ppmw to 2,000 ppmw of sodium ions.

And, the concentration of the anions in the electrolyte included in the second electrolyte compartment may be identical to the concentration of the anions in the electrolyte included in the electrolyte compartment (first electrolyte compartment). Thereby, as the concentrations of the anions in the electrolytes contacting both sides of the polymer film become identical, flowability of current by the electrolyte may be improved, and fine current flow change that is generated in case a trace amount of metal ions penetrate a polymer insulation film can be easily measured with high reproducibility.

The first electrolyte and second electrolyte may comprise anions, organic solvents, and aqueous solvents together with metal ions, and the above explained with regard to the electrolyte compartment (corresponding to the first electrolyte compartment) or electrolyte (corresponding to the first electrolyte) applies to the organic solvent, aqueous solvent.

The above explained with regard to the electrolyte compartment (corresponding to the first electrolyte compartment) applies to the material, thickness of the partition walls (side walls) of the second electrolyte compartment (8).

Here, the polymer film mounting part (3) may further comprise a fixing tool that closely contacts the first electrolyte compartment (4), the second electrolyte compartment (8), and the polymer film mounted on the polymer film mounting part (3) with each other, and fixes them.

Specific shape or practical fastening method or structure of the fixing tool (7) is not significantly limited, and for example, a fixing tool (jig) of a structure that can be added to the rear side of the external protrusion part of the polymer film mounting part may be used, a hole penetrating the fixing tool and the external protrusion part of the polymer film mounting part may be connected with a screw to press, and both ends of a belt-shaped structure with a groove of an oblique angle covering the external protrusion part of the polymer film mounting part may be fixed with a screw to press.

The device for measuring metal ion permeability of a polymer film comprises a voltage applying part that is connected with the first electrode and the second electrode, and applies a voltage.

The size of the voltages applied to the first electrode and second electrode is not significantly limited, and it may be selected within a range of 0.001 V to 100 V considering the kind of the polymer film or measured value of current change or resistance change.

The device for measuring metal ion permeability of a polymer film comprises an electrical signal measuring part that measures resistance change or current change of the polymer film mounted on the polymer film mounting part.

In the device for measuring metal ion permeability of a polymer film of the above embodiment, if voltages are applied to the first electrode and second electrode, metal ions positioned in the electrolyte compartments move by current, and thus, when the metal ions penetrate the polymer film positioned on the polymer film mounting part, current flows and resistance becomes low, thus generating an electrical signal.

Thus, in the above embodiment, the metal ion permeability of a polymer film may be measured as a rate of change of resistance or a rate of change of current according to time, said change beginning to appear when the metal ions begin to penetrate the polymer film, after a voltage is applied to the polymer film to be measured.

Specifically, the metal ion permeability of a polymer film may be determined as a time until the first time (T) at which the change rate of current or resistance according to time is constantly maintained, from the time at which a predetermined voltage (for example, 0.1 V to 10.0 V) is applied.

The meaning of the description "the change rate of current or resistance according to time is constantly maintained" includes a case wherein, in the corresponding time interval, the change rate of current or resistance according to time is included in a range within 25% of the mean value of the change rate of current or the change rate of resistance according to time, and a case wherein the change ratio of instantaneous rate of change of current or resistance according to time (or the change ratio of the differential value of change of current or resistance according to time) becomes 0, etc.

The first time (T) at which the change rate of current or resistance according time is constantly maintained means a first time at which the change of current or resistance according to time becomes constant, after the change of current or resistance according time occurs, and it may appear after passing an inflection point of the change of current or resistance according time.

The first time (T) may be determined as a first time at which the change ratio of the instantaneous rate of change of current or resistance according to time (or the change ratio of the differential value of current of resistance change according to time) becomes 0, or as a first time in a time interval in which the change rate of current or resistance according to time is included in a range within 25% of the mean value of the change rate of current or the change rate of resistance according to time.

For the determination of the first time, various methods can be used without specific limitations, and for example, it may be determined by calculating the average change rate of current or resistance according to time in the corresponding time interval, and extrapolating a time at which the average change rate value appears, after passing an inflection point of current or resistance change according to time.

Although the range of change rate of current or change rate of resistance that can be measured by the measurement device of metal ion permeability of a polymer film of the above embodiment is not significantly limited, for example, in case a voltage of 0.1 V to 10.0 V is applied to the measurement device, the first time at which the change of current or resistance becomes constant, after change of current or resistance according to time appears, may be 8 hours or less, or 0.5 hours to 8 hours.

Meanwhile, the metal ion permeability may be represented by the change rate of current or resistance according time, and specifically, it may be the average rate of change of current of resistance according to time, after the first time (T), and for example, it may be A/10 seconds, A/1 minutes, A/1 hour, A/10 hours, $\Omega$/10 seconds, $\Omega$/1 minute, $\Omega$/1 hour, $\Omega$/10 hours, etc.

More specifically, if a polymer film of which metal ion permeability is to be measured is positioned on the polymer film mounting part (3), the electrolyte comprising metal ions in the electrolyte compartment (4) contacts with one side of the polymer film. And, while one side of the polymer film contacts with the electrolyte comprising metal ions, voltages are applied to a second electrode that is in contact with the other side of the polymer film and to a first electrode that opposes the second electrode and is in contact with the electrolyte, using a voltage applying part (5) that is connected to the first electrode and second electrode and applies voltages, and thereafter, the change of resistance or change of current of the polymer film mounted on the polymer film mounting part is measured using an electrical signal measuring part (6).

Alternatively, if a polymer film of which metal ion permeability is to be measured is positioned on the polymer film mounting part (3), the electrolyte (first electrolyte) comprising metal ions in the first electrolyte compartment (4) contacts with one side of the polymer film, and the electrolyte (second electrolyte) in the second electrolyte compartment (8) contacts with the other side of the polymer film. And, while both sides of the polymer film respectively contact with the electrolyte comprising metal ions and the electrolyte, voltages are applied to the first electrode and the second electrode using a voltage applying part (5), and thereafter, the change of resistance or change of current of the polymer film mounted on the polymer film mounting part is measured using an electrical signal measuring part (6).

Specific kind or structure of the electrical signal measuring part is not significantly limited, devices capable of measuring change of resistance or change of current generated in the polymer film to be measured after applying a voltage may be used without significant limitations, and for example, devices such as a potentiostat, etc. may be used.

The device for measuring metal ion permeability of a polymer film of the above embodiment may further comprise a chamber including an internal space in which the first electrode, second electrode, electrolyte compartment, and polymer film mounting part are positioned. The electrolyte compartment includes the first electrolyte compartment (4) or the second electrolyte compartment (8).

The voltage applying part; and the electrical signal measuring part (6) may be positioned inside or outside the chamber, and it may be installed in the chamber itself.

As the chamber, reaction chambers made of commonly known material may be used, and the shape or structure of the chamber is not significantly limited.

And, the chamber may further comprise a temperature control part and a humidity control part.

The temperature inside the chamber may be 0° C. to 400° C., and through the temperature control part installed in the chamber, the temperature in the process of measuring metal ion permeability of a polymer film may be controlled. Specific structure or kind of the temperature control part is not significantly limited, and for example, it may include devices such as a convection oven, a HAST([Highly Accelerated Stress Test] oven or a PCT (Pressure Cooker Test) oven, etc.

In case the device for measuring metal ion permeability of a polymer film is operated to measure metal ion permeability, the temperature inside the chamber may be 5° C. to 250° C., or 20° C. to 200° C.

In case the device for measuring metal ion permeability of a polymer film is operated to measure metal ion permeability, the pressure inside the chamber may be 1 atm to 5 atm.

Meanwhile, although the kind of polymer films that can be applied for the device for measuring metal ion permeability of a polymer film is not significantly limited, polymer films having insulation property may be the main subjects of the measurement of metal ion permeability. Specifically, the polymer films that can be applied for the device for measuring metal ion permeability of a polymer film may include a die bonding film, a solder resist, a bonding sheet for a substrate, an insulation film, etc.

Meanwhile, according to still another embodiment of the present invention, a device for measuring metal ion permeability of a polymer film, for use in the method for measuring metal ion permeability of a polymer film of one embodiment, is provided.

The above explained applies to the method for measuring metal ion permeability of a polymer film and the operation device thereof.

Hereinafter, the present disclosure will be explained in detail with reference to the following examples. However, these examples are only to illustrate the inventive concept, and the scope of the inventive concept is not limited thereto.

Preparation Examples 1 to 3: Preparation of an Adhesive Film Having Insulation Property (1) Preparation of a Solution of a Resin Composition Phenol resin, epoxy resin, acrylic resin, a cure accelerator, a coupling agent, and a filler were dissolved in methylethylketone with the contents described in the following Table 1, to obtain a solution of an adhesive resin composition for semiconductor (solid content 20 wt %).

(2) Preparation of an Adhesive Film

The above prepared solution of an adhesive resin composition for semiconductor was coated on a polyethylene terephthalate film (thickness 38 μm), and then, dried at 130° C. for 3 minutes to obtain an adhesive film with a thickness of 20 μm. The glass transition temperature (TMA measurement) and modulus (DMA measurement) of each adhesive film of Preparation Examples 1 to 3 were measured, and the results are shown in the following Table 2.

TABLE 1

| Composition of a solution of a resin composition [unit: g] | | | | |
|---|---|---|---|---|
| components | | Preparation Example 1 | Preparation Example 2 | Preparation Example 3 |
| Phenol resin | KPH-F2001 | 50 | — | 50 |
| | KH-6021 | — | 50 | — |
| Epoxy resin | EOCN-104S | 100 | 100 | — |
| | HP-7200 | — | — | 100 |
| Acrylic resin | KG-3037 | 500 | 500 | 500 |
| Cure accelerator | 2P4MHZ | 0.5 | 0.5 | 0.5 |
| Coupling agent | KBM-403 | 2 | 2 | 2 |
| Filler | RY-50 | 90 | 90 | 90 |

KPH-F2001: phenol novolac resin (Kolon Chemical Co., Ltd., hydroxyl equivalent: 106 g/eq, softening point: 88° C.)
KH-6021: bisphenolA novolac phenol resin (DIC Corp, hydroxyl equivalent: 118 g/eq, softening point: 133° C.)
EOCN-104S: cresol novolac phenol resin (Nippon Kayaku, epoxy equivalent: 214 g/eq, softening point: 92° C.)
HP-7200: DCPD-based novolac phenol resin (DIC Corp, epoxy equivalent: 257 g/eq, softening point: 62° C.)
KG-3037: acrylate-based resin (glycidyl methacrylate-based repeat units 13 wt %, glass transition temperature: 20° C., Mw 800,000)
2P4MHZ: 2-phenyl-4-methyl-5-dihydroxymethyl imidazole (Shikoky Chemical Corp.)
KBM-403: gamma-glycidoxy propyl trimethoxy silane (Shin-etsu Chemical Co., Ltd.)
RY-50: spherical silica (Evonik, average particle diameter 40 nm)

TABLE 2

| Properties of adhesive films | | | |
|---|---|---|---|
| | Preparation Example 1 | Preparation Example 2 | Preparation Example 3 |
| Glass transition temperature(° C.) | 180 | 170 | 165 |
| Modulus (MPa) | 5 | 4 | 5 |

Examples 1 to 2: Manufacture of a Device for Measuring Metal Ion Permeability of a Polymer Film Example 1

Figure 2:
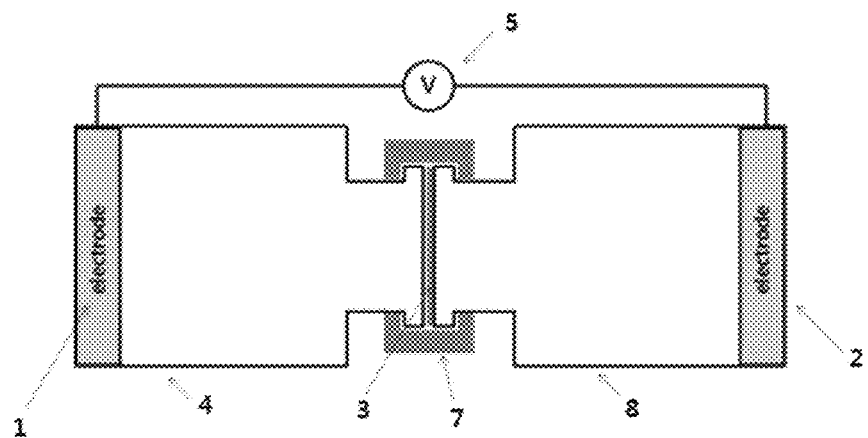
FIG. 2 schematically shows another example of a device for measuring metal ion permeability of a polymer film of the present invention.
Figure 3:
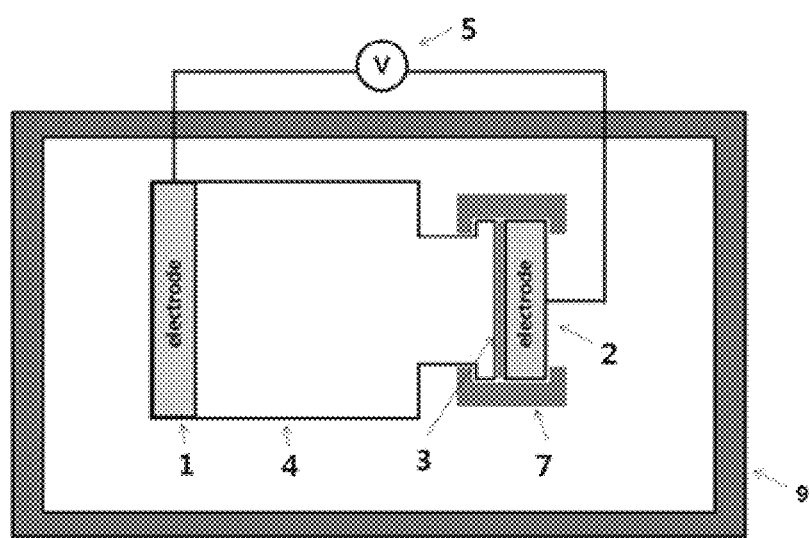
FIG. 3 schematically shows still another example of a device for measuring metal ion permeability of a polymer film of the present invention.
Figure 4:
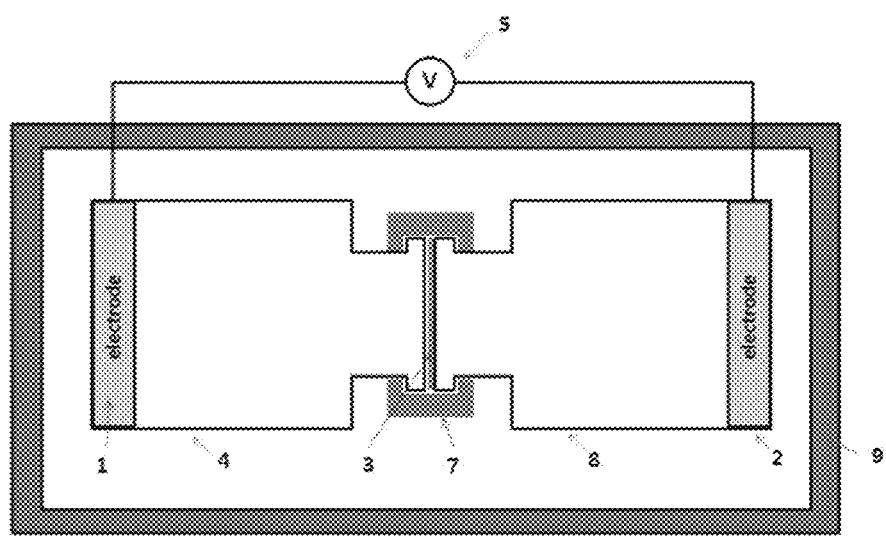
FIG. 4 schematically shows still another example of a device for measuring metal ion permeability of a polymer film of the present invention.
Figure 5:
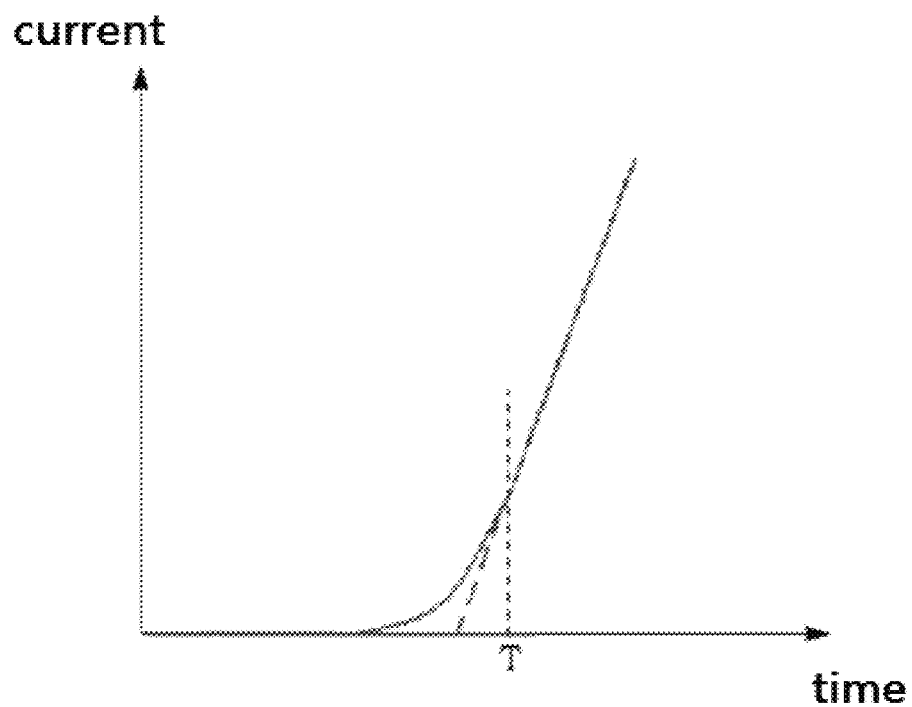
FIG. 5 is a graph showing the change of current according to time, after applying a voltage to a device for measuring metal ion permeability of a polymer film of Example.

As shown in FIG. 2, a device for measuring metal ion permeability of a polymer film comprising: a first electrode and a second electrode opposing each other; a first electrolyte compartment that is in contact with the first electrode, and includes an electrolyte comprising metal ions inside; a second electrolyte compartment that is in contact with one side of the second electrode and includes electrolyte; a polymer film mounting part that is defined as a space between the first electrolyte compartment and the second electrolyte compartment; a voltage applying part that is connected with the first electrode and the second electrode, and applies a voltage; and an electrical signal measuring part that measures resistance change or current change of the polymer film mounted in the polymer film mounting part, was manufactured.

Example 2

As shown in FIG. 1, a device for measuring metal ion permeability of a polymer film comprising: a first electrode and a second electrode opposing each other; a polymer film mounting part that is installed in such a way that one side of the first electrode is in contact with a polymer resin film; an electrolyte compartment that is positioned between the second electrode and the polymer film mounting part, and includes a dimethylsulfoxide (DMSO) electrolyte aqueous solution containing 1000 ppm of copper ions inside; a voltage applying part that is connected with the first electrode and the second electrode, and applies a voltage; and an electrical signal measuring part that measures resistance change or current change of the polymer film mounted in the polymer film mounting part, was manufactured.

Examples 3 to 14: A Method for Measuring Metal Ion Permeability of a Polymer Film

Example 3

On the device for measuring metal ion permeability of a polymer film manufactured in Example 1, the adhesive film with a thickness of 20 μm obtained in Preparation Example 1 was mounted, and at room temperature and atmospheric pressure, as shown in FIG. 2, in the first electrolyte compartment, a first solvent comprising water ($H_2O$) and dimethyl sulfoxide (DMSO) at a weight ratio of 1:1 was filled such that the concentration of copper sulfate ($Cu_2SO_4$) became 1000 ppmw, and water ($H_2O$) and dimethyl sulfoxide were filled at a weight ratio of 1:1 such that the concentration of sodium sulfate ($Na_2SO_4$) became 1000 ppmw, and then, while applying a voltage of 10 V, the first time at which the change of current or resistance according to time became constant, after the change of current or resistance according to time occurred, was judged as the end time of measurement. And, a time (T) until the measurement end time from the time at which the voltage is applied, was calculated, and measurement efficiency of metal ion permeability was evaluated according the following standard.

Excellent: The T value is measured within 8 hours
Faulty: The T value is measured to be greater than 8 hours

Examples 4 to 8

Metal ion permeability was measured by the same method as Example 3, except that the kind of a measurement device, the kind of an adhesive film, a measurement temperature, the weight ratio of $H_2O$:DMSO in the first solvent and the second solvent contained in the electrolytes varied as described in the following Table 3,

Examples 9 to 14

Metal ion permeability was measured by the same method as Example 3, except that, as shown in the following Table 3, the device for measuring metal ion permeability of a polymer film manufactured in Example 2 was used, and at room temperature and atmospheric pressure, as shown in FIG. 1, in the electrolyte compartment, water ($H_2O$) and dimethyl sulfoxide (DMSO) were filled at each weight ratio, such that the concentration of copper sulfate ($Cu_2SO_4$) became 1000 ppmw.

TABLE 3

Measurement conditions and results of metal ion permeability of Examples 3 to 14

| | Measurement device | Adhesive film | Measurement temperature (° C.) | Ratio of $H_2O$:DMSO | Measurement end time (H) | Efficiency evaluation Result |
|---|---|---|---|---|---|---|
| Example3 | Example 1 | Preparation Example 1 | Room temperature | 1:1 | 3.2 | Excellent |
| Example4 | | Preparation Example 2 | | | 2.6 | Excellent |
| Example5 | | Preparation Example 3 | | | 3.7 | Excellent |
| Example6 | | Preparation Example 1 | | 7:3 | 4.5 | Excellent |
| Example7 | | Preparation Example 2 | | | 4.1 | Excellent |
| Example8 | | Preparation Example 3 | | | 5.1 | Excellent |
| Example9 | Example 2 | Preparation Example 1 | | 1:1 | 5.2 | Excellent |
| Example10 | | Preparation Example 2 | | | 4.2 | Excellent |
| Example 11 | | Preparation Example 3 | | | 5.6 | Excellent |
| Example 12 | | Preparation Example 1 | | 7:3 | 7.4 | Excellent |
| Example 13 | | Preparation Example 2 | | | 6.1 | Excellent |
| Example 14 | | Preparation Example 3 | | | 7.9 | Excellent |

As shown in Table 3, in the case of the method of measuring metal ion permeability of Examples 3 to 14, by evaluating the reliability of an adhesive film by metal ion permeability, it could be rapidly measured within 8 hours under various conditions, and the reproducibility of the measurement results appeared excellent.

Comparative Examples 1 to 22: Measurement of Metal Ion Permeability of a Polymer Film Comparative Example 1

On a flexible copper circuit board, the adhesive film obtained in Preparation Example 1 was mounted such that the comb-shaped electrodes cross each other, and while applying voltage of 3V to both electrodes under the conditions of 110° C., 85% RH, insulation resistance value between the electrodes according to time was measured, and the moment at which the insulation resistance value between the electrodes became lower than $1\times10^5\Omega$ was judged as an end time of measurement. And, a time (T') until the end time of measurement from the time at which voltage was applied was calculated, and measurement efficiency of metal ion permeability was evaluated according to the following standards.

Excellent: The T' value is measured to be within 8 hours
Faulty: The T' value is measured to be greater than 8 hours Comparative Examples 2 to 18

Metal ion permeability was measured by the same method as Comparative Example 1, except that the kind of adhesive films, measurement temperature, and applied voltage varied as shown in the following Table 4.

TABLE 4

Measurement conditions and results of metal ion permeability of Comparative Examples 1 to 18

| | Adhesive film | Measurement Temperature (° C.) | Applied Voltage (V) | Measurement end time (H) | Efficiency evaluation Result |
|---|---|---|---|---|---|
| Comparative Example 1 | Preparation Example 1 | 10 | 3 | 345 | Faulty |
| Comparative Example 2 | Preparation Example 2 | | 3 | 285 | Faulty |
| Comparative Example 3 | Preparation Example 3 | | 3 | 393 | Faulty |
| Comparative Example 4 | Preparation Example 1 | | 10 | 211 | Faulty |
| Comparative Example 5 | Preparation Example 2 | | 10 | 183 | Faulty |
| Comparative Example 6 | Preparation Example 3 | | 10 | 244 | Faulty |
| Comparative Example 7 | Preparation Example 1 | | 20 | 155 | Faulty |
| Comparative Example 8 | Preparation Example 2 | | 20 | 127 | Faulty |
| Comparative Example 9 | Preparation Example 3 | | 20 | 171 | Faulty |
| Comparative Example 10 | Preparation Example 1 | 130 | 3 | 247 | Faulty |
| Comparative Example 11 | Preparation Example 2 | | 3 | 210 | Faulty |
| Comparative Example 12 | Preparation Example 3 | | 3 | 280 | Faulty |
| Comparative Example 13 | Preparation Example 1 | | 10 | 130 | Faulty |
| Comparative Example 14 | Preparation Example 2 | | 10 | 115 | Faulty |
| Comparative Example 15 | Preparation Example 3 | | 10 | 145 | Faulty |
| Comparative Example 16 | Preparation Example 1 | | 20 | 95 | Faulty |
| Comparative Example 17 | Preparation Example 2 | | 20 | 83 | Faulty |
| Comparative Example 18 | Preparation Example 3 | | 20 | 105 | Faulty |

As shown in Table 4, in the case of Comparative Examples, since the reliability of an adhesive film was evaluated by a high temperature, high humidity HAST method, even if conditions were modified, the end time of measurement became significantly long such as greater than 50 hours, etc., and thus, it could be confirmed that measurement efficiency are very bad.

That is, in the case of metal ion permeation of an adhesive film according to Examples, evaluation results can be confirmed within a short time compared to the conventional reliability evaluation method of an adhesive film, and thus, measurement efficiency can be further improved, and the reproducibility of measurement results appears excellent.

Comparative Examples 19 to 22

As shown in the following Table 5, metal ion permeability was measured by the same method as Example 3, except that the kind of a measurement device, the kind of an adhesive film, a measuring temperature, and the weight ratio of $H_2O$:DMSO in the first solvent and second solvent contained in the electrolyte varied as shown in the following Table 5.

TABLE 5

Measurement conditions and results of metal ion permeability of Comparative Examples 19 to 22

| | Measurement device | Adhesive film | Measurement Temperature (° C.) | $H_2O$:DMSO ratio | End time of measurement (H) | Efficiency Evaluation result |
|---|---|---|---|---|---|---|
| Comparative Example 19 | Example1 | Preparation Example1 | Room temperature | 9:1 | 18.3 | faulty |
| Comparative Example 20 | | Preparation Example2 | | | 14.5 | faulty |
| Comparative Example 21 | | Preparation Example3 | | | 25.5 | faulty |

As shown in Table 5, in case the ratio of $H_2O$:DMSO is 9:1 and the content of the organic solvent excessively decreases, the end time of measurement significantly prolonged to greater than 10 hours, and it could be confirmed that measurement efficiency is very bad.

DESCRIPTION OF SYMBOLS

1—first electrode
2—second electrode
3—polymer film mounting part
4—first electrolyte compartment
5—voltage applying part
6—electrical signal measuring part
7—fixing tool
8—second electrolyte compartment
9—chamber

What is claimed is:

1. A method for measuring metal ion permeability of a polymer film, comprising the steps of:
applying a voltage to the polymer film using a device, while at least one side of the polymer film is brought into contact with an electrolyte comprising metal ions, an organic solvent and an aqueous solvent, wherein the device comprises: a first electrode and a second electrode opposing each other; an electrolyte compartment that is in contact with the first electrode, and includes an electrolyte comprising metal ions, an organic solvent and an aqueous solvent inside; a polymer film mounting part that is positioned between the second electrode and the electrolyte compartment, and is installed in such a way that the electrolyte included in the electrolyte compartment is in contact with a polymer resin film; a voltage applying part that is connected with the first electrode and the second electrode, and applies a voltage; and an electrical signal measuring part that measures resistance change or current change of the polymer film mounted in the polymer film mounting part; and
measuring using the electrical signal measuring part of the device a change rate of resistance or change rate of current of the polymer film according to time, by measuring a time until a first time (T) at which the change rate of current or the change rate of resistance according to time is constantly maintained, after the voltage is applied, thereby measuring the metal ion permeability of the polymer film as an average rate of change of current or the change rate of resistance according to time, after the first time (T).

2. The method of claim 1, wherein the first time at which the change rate of current or the change rate of resistance according to time is constantly maintained, is the first time of a time interval in which the change rate of current or the change rate of resistance according to time is included in a range within 25% of a mean value of the change rate of current or the change rate of resistance according to time, or
the first time at which a change ratio of a differential value of change of current or resistance according to time becomes 0, after passing an inflection point of change of current or change of resistance according to time.

3. The method of claim 1, wherein the time until the first time (T) at which the change rate of current or the change rate of resistance according time is constantly maintained, after the voltage is applied, is 8 hours or less.

4. The method of claim 3, wherein the time until the first time (T) at which the change rate of current or the change rate of resistance according to time is constantly maintained, after the voltage is applied, is measured at room temperature, atmospheric pressure and an applied voltage of 10V.

5. The method of claim 1, wherein the electrolyte comprises 20 to 200 parts by weight of the organic solvent, based on 100 parts by weight of the aqueous solvent.

6. The method of claim 1, wherein a boiling point of the organic solvent included in the electrolyte is higher than a temperature of the step of applying the voltage to the polymer film.

7. The method of claim 1, wherein the organic solvent included in the electrolyte comprises a sulfoxide organic solvent.

8. The method of claim 7, wherein the sulfoxide organic solvent comprises dialkyl sulfoxide having a carbon number of 1 to 3.

9. The method of claim 1, wherein concentrations of the metal ions included in the electrolyte are from 0.1 ppmw to 2,000 ppmw.

10. The method of claim 1, wherein the metal ions include one or more metal ions selected from the group consisting of copper, gold, platinum, silver, iron, mercury, potassium, calcium, sodium, aluminum, nickel and chromium.

11. The method of claim 1, wherein the step of applying the voltage to the polymer film while the at least one side of the polymer film is brought into contact with the electrolyte comprising the metal ions, the organic solvent and the aqueous solvent, comprises a step of applying a voltage while one side of the polymer film is brought into contact with the electrolyte comprising the metal ions.

12. The method of claim 11, wherein the step of applying the voltage while the one side of the polymer film is brought into contact with the electrolyte comprising the metal ions, comprises a step of applying a voltage to a first electrode and a second electrode, the first electrode opposing the second electrode and in contact with the electrolyte, and the second electrode in contact with other side of the polymer film.

13. The method of claim 1, wherein the step of applying the voltage while the at least one side of the polymer film is brought into contact with the electrolyte comprising the metal ions, comprises a step of applying a voltage to the polymer film, while one side of the polymer film is brought into contact with a first electrolyte comprising metal ions and other side of the polymer film is brought into contact with a second electrolyte.

14. The method of claim 13, wherein the step of applying the voltage to the polymer film, while the one side of the polymer film is brought into contact with the first electrolyte comprising the metal ions and the other side of the polymer film is brought into contact with the second electrolyte, comprises a step of applying a voltage to a first electrode and a second electrode, the first electrode in contact with the first electrolyte comprising the metal ions, and the second electrode opposing the first electrode and in contact with the second electrolyte.

15. The method of claim 13, wherein the metal ions included in the first electrolyte are different from metal ions included in the second electrolyte.

16. The method of claim 15, wherein the concentrations of the metal ions included in the first electrolyte and the second electrolyte are respectively 0.1 ppmw to 2,000 ppmw.

17. A device for measuring metal ion permeability of a polymer film, for use in the method for measuring metal ion permeability of the polymer film of claim 1.

18. A device for measuring metal ion permeability of a polymer film comprising:
a first electrode and a second electrode opposing each other;
an electrolyte compartment that is in contact with the first electrode, and includes an electrolyte comprising metal ions, an organic solvent and an aqueous solvent inside;
a polymer film mounting part that is positioned between the second electrode and the electrolyte compartment, and is installed in such a way that the electrolyte included in the electrolyte compartment is in contact with a polymer resin film;
a voltage applying part that is connected with the first electrode and the second electrode, and applies a voltage; and
an electrical signal measuring part that measures resistance change or current change of the polymer film mounted in the polymer film mounting part, wherein the metal ion permeability of the polymer film is defined as an average rate of change of current or the change rate of resistance according to time, after the first time (T).

19. The device of claim 18, wherein the polymer film mounting part is installed in such a way that one side of the second electrode is in contact with a polymer resin film.

20. The device of claim 19, wherein the polymer film mounting part further comprises a fixing tool that closely contacts and fixes the second electrode, the polymer film mounted on the polymer film mounting part, and the electrolyte compartment with one another.

21. The device of claim 18, further comprising a second electrolyte compartment that is positioned between the second electrode and the polymer film mounting part, is in contact with the second electrode, and includes an electrolyte comprising metal ions, an organic solvent and an aqueous solvent inside.

22. The device of claim 21, wherein the electrolyte included in the second electrolyte compartment comprises 0.1 ppmw to 2,000 ppmw of metal ions.

23. The device of claim 21, wherein the metal ions in the electrolyte included in the second electrolyte compartment are different from the metal ions in the electrolyte included in the electrolyte compartment.

24. The device of claim 21, wherein the polymer film mounting part further comprises a fixing tool that closely contacts and fixes the first electrolyte compartment, the second electrolyte compartment, and the polymer film mounted on the polymer film mounting part with one another.

25. The device of claim 18, wherein the electrical signal measuring part is a device that measures the change rate of resistance or the change rate of current according to time of the polymer film mounted on the polymer film mounting part, after applying voltages to the first electrode and the second electrode using the voltage applying part.

* * * * *